United States Patent
Tanaka et al.

(10) Patent No.: US 8,029,613 B2
(45) Date of Patent: Oct. 4, 2011

(54) ONE-PACK TYPE DENTAL ADHESIVE COMPOSITION

(75) Inventors: Hisaki Tanaka, Kyoto (JP); Toshihide Fujii, Kyoto (JP); Yutaka Yamaguchi, Kyoto (JP); Mikito Deguchi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 84 days.

(21) Appl. No.: 12/585,974

(22) Filed: Sep. 30, 2009

(65) Prior Publication Data

US 2010/0101453 A1   Apr. 29, 2010

(30) Foreign Application Priority Data

Oct. 23, 2008   (JP) ................................ 2008-272887

(51) Int. Cl.
*C09K 3/00* (2006.01)
*A61K 6/00* (2006.01)
(52) U.S. Cl. ......................... 106/35; 523/118
(58) Field of Classification Search .................... 106/35; 523/118
See application file for complete search history.

(56) References Cited

U.S. PATENT DOCUMENTS

| 4,380,432 | A  | * | 4/1983 | Orlowski et al. | .................. 433/9 |
| 5,489,625 | A  | * | 2/1996 | Moriwaki et al. | ............. 523/118 |
| 6,217,644 | B1 | * | 4/2001 | Matsunae et al. | ................ 106/35 |
| 2007/0155853 | A1 | * | 7/2007 | Chen et al. | ..................... 523/109 |

* cited by examiner

*Primary Examiner* — Shuangyi Abu Ali
(74) *Attorney, Agent, or Firm* — Wenderoth, Lind & Ponack, L.L.P.

(57) ABSTRACT

Disclosed is a one-pack type dental adhesive composition comprising:
(a) 1.0 to 40.0 parts by weight of a silane coupling agent,
(b) 0.01 to 0.4 part by weight of a weak acidic compound which is at least one of organic acid, boric acid and silicic acid, and has an acid dissociation exponent pKa of 3 or more in the form of an aqueous solution,
(c) 0.01 to 0.4 part by weight of a strong acidic compound which is at least one of HF, HCl, HBr, HI, $HNO_3$, $HClO_3$, $HClO_4$, $HBrO_4$, $HMnO_4$, $H_2SO_4$ and $H_3PO_4$ and has an acid dissociation exponent pKa of less than 3,
(d) 0.1 to 5.0 part by weight of water, and
(e) 20.0 to 99.0 parts by weight of a volatile organic solvent.

1 Claim, No Drawings

ONE-PACK TYPE DENTAL ADHESIVE COMPOSITION

BACKGROUND OF THE INVENTION

1. Field of the Invention

The present invention relates to a one-pack type dental adhesive composition which can exhibit excellent adhesion to any material such as dental ceramics, or an organic composite containing an inorganic compound (hereinafter, referred to as composite material in some cases), and is also excellent in storage stability.

2. Description of the Related Art

As a dental restorative material, dental ceramics or an organic composite containing an inorganic compound is often used. Typical examples of the dental restorative material include a dental porcelain (containing silicon dioxide as a main component), alumina, zirconia, and a composite material.

In the adhesion, it is known that a trial of improving adhesion is made by a composition containing a silane coupling agent as a main component. An acidic compound is required so as to improve adhesion, together with a silane coupling agent, and a composition incorporating both a silane coupling agent and an acidic compound therein is commercially available.

However, since a silane coupling agent and an acidic compound usually cannot be stored in the same solvent over a long period, two kinds of materials must be mixed immediately before use. Therefore, there has been required a material which does not require time for mixing before use, and is also excellent in storage stability.

Although a composition containing a silane coupling agent, an acid, water and a solvent is known from Japanese Patent No. 2,730,677, the composition contains a small amount of a silane coupling agent and a sufficient adhesive strength cannot be obtained.

SUMMARY OF THE INVENTION

An object of the present invention is to exhibit excellent adhesion to any material such as dental ceramics, or an organic composite containing an inorganic compound. Another object of the present invention is to provide a dental adhesive composition having satisfactory operability, which accounts for the majority of requirements of users, for the purpose of reducing an operation time and a technical error, namely, a one-pack type dental adhesive composition.

Thus, a main object of the present invention is to provide a one-pack type dental adhesive composition in the form of a solution containing a silane coupling agent, an acidic compound and water.

That is, the present invention provides a one-pack type dental adhesive composition comprising:

(a) 1.0 to 40.0 Tarts by weight of a silane coupling agent, (b) 0.01 to 0.4 part by weight of a weak acidic compound which is at least one of organic acid, boric acid and silicic acid, and has an acid dissociation exponent pKa of 3 or more in the form of an aqueous solution, (c) 0.01 to 0.4 part by weight of a strong acidic compound which is at least one of HF, HCl, HBr, HI, $HNO_3$, $HClO_3$, $HClO_4$, $HBrO_4$, $HMnO_4$, $H_2SO_4$ and $H_3PO_4$ and has an acid dissociation exponent pKa of less than 3, (d) 0.1 to 5.0 part by weight of water, and (e) 20.0 to 99.0 parts by weight of a volatile organic solvent.

By employing such a constitution, the one-pack type dental adhesive composition of the present invention imparts excellent adhesion, which has never been attained, and durability thereof to each of dental ceramics, and an organic composite containing an inorganic compound, and exhibits simple operability, and is also excellent in storage stability.

The silane coupling agent (a) is represented by the following general formula [1]:

[Chemical Formula 1]

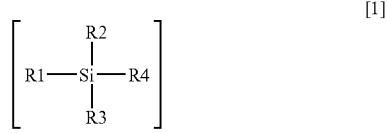

wherein R1 represents an organic residue having at least one functional group selected from the group consisting of a (meth)acryloyl group, a vinyl group, a styryl group, a mercapto group and an epoxy group; R2 represents a hydroxyl group, an alkyl group having 1 to 5 carbon atoms, or an alkoxy group having 1 to 5 carbon atoms; and R3 and R4 each represents a hydroxyl group or an alkoxy group having 1 to 5 carbon atoms.

The silane coupling agent (a) is preferably a compound represented by the general formula [1] in which R1 is an organic residue having at least one functional group selected from the group consisting of a (meth)acryloyl group and a vinyl group; R2 is a hydroxyl group, an alkyl group having 1 to 5 carbon atoms, or an alkoxy group having 1 to 5 carbon atoms; and R3 and R4 each is a hydroxyl group or an alkoxy group having 1 to 5 carbon atoms.

The weak acidic compound (b) is in the form of an aqueous solution and has an acid dissociation exponent pKa of 3 or more, and is organic acid, boric acid or silicic acid. Specific examples thereof include formic acid, acetic acid, propionic acid, benzoic acid, phenol, and carbonic acid.

The strong acidic compound (c) is in the form of an aqueous solution-based and has an acid dissociation exponent pKa of less than 3. Specific examples thereof include HF, HCl, HBr, HI, $HNO_3$, $HClO_2$, $HClO_4$, $HBrO_4$, $HMnO_4$, $H_2SO_4$, and $H_3PO_4$.

Examples of the volatile organic solvent (e) include methanol, ethanol, isopropanol, butanol, acetone, ethyl acetate, isopropylether, and a radical polymerizable monomer such as a (meth)acrylic acid ester, (meth)acrylamide, a vinyl ester or the like.

The dental adhesive composition of the present invention imparts excellent adhesion and durability to any material such as dental ceramics, or an organic composite containing an inorganic compound, and is excellent in storage stability, and also exhibits simple operability.

Specifically, the dental adhesive composition of the present invention is used for adhesion to a resin-based material when any one of a dental restoration, a dental restorative material and a dental device is made of dental ceramics, or an organic composite containing an inorganic compound in mutual adhesion of any one of a dental restoration, a dental restorative material and a dental device.

Since the dental adhesive composition of the present invention is a one-pack type adhesive composition, operation is simple. In a conventional two-pack mixing type product, a mixing operation is required, resulting in complicated operation and loss in an operation time. Furthermore, the product requires security of a proper mixing ratio of two liquids and it is unclear whether or not sufficient mixing operation is performed, resulting in a technical error and loss. The dental adhesive composition of the present invention can also be used as a primer, and also can be used in combination with another adhesive.

DETAILED DESCRIPTION OF THE INVENTION

Specific embodiments in the dental adhesive composition of the present invention are a one-pack type dental ceramics or an organic composite adhesive primer containing an inorganic compound, a dental adhesive, an adhesive composite resin and a resin cement.

In use of dental ceramics or an organic composite adhesive one-pack type primer containing an inorganic compound, high adhesion can be exhibited by very simple treatment. The adhesive composition of the present invention can be used for a dental bonding agent, an adhesive composite resin, an orthodontic adhesive, a resin cement, a dual cure type resin cement, an opaque agent, a compomer, a resin core, a facing crown material or the like as an aspect thereof.

It is important to use, as the silane coupling agent (a) in the present invention, a silane coupling agent having functional groups which can copolymerize with a polymerizable monomer component in an adhesive composition and/or an adherend material, or can form a chemical bond so as to obtain good adhesion to a ceramic material.

In the present invention, as the silane coupling agent which satisfies this condition, a silane compound represented by the general formula (1) is used. Among functional groups of R1, a (meth)acryloyl group, a vinyl group and a styryl group are connected to a polymer of a (meth)acrylic acid ester monomer by copolymerization with the (meth)acrylic acid ester monomer. A mercapto group is connected to a polymer of a (meth)acrylic acid ester monomer by formation of a chemical bond derived from chain transfer/termination reaction. An epoxy group is connected to a polymer of a (meth)acrylic acid ester monomer by forming a chemical bond with a monomer having an amino group or carboxyl group which can react with the epoxy group. In order to quickly condense a silane coupling agent with a silanol group of a surface of an adherend, R2, R3 and R4 each preferably represents a lower alkoxy or hydroxyl group having 1 to 5 carbon atoms. R2 may be an alkyl group having 1 to 5 carbon atoms. Specific examples of the silane coupling agent, which satisfies the above conditions, include the followings.

[Chemical Formula 2]

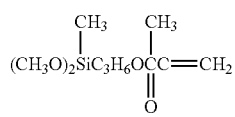

3-Methacryloxypropylmethyldimethoxysilane

[Chemical Formula 3]

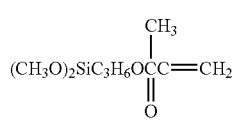

3-Methacryloxypropyltrimethoxysilane

[Chemical Formula 4]

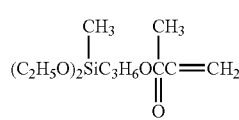

3-Methacryloxypropylmethyldiethoxysilane

[Chemical Formula 5]

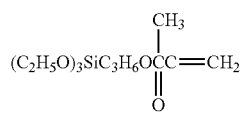

3-Methacryloxypropyltriethoxysilane

[Chemical Formula 6]

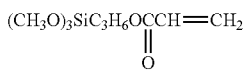

3-Acryloxypropyltrimethoxysilane

[Chemical Formula 7]

$(CH_3O)_3SiCH{=}CH_2$

Vinyltrimethoxysilane

[Chemical Formula 8]

$(C_2H_5O)_3SiCH{=}CH_2$

Vinyltriethoxysilane

[Chemical Formula 9]

p-styryltrimethoxysilane

[Chemical Formula 10]

$(CH_3O)_3SiC_3H_6SH$

3-Mercaptopropyltrimethoxysilane

[Chemical Formula 11]

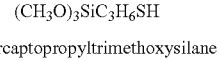

3-Mercaptopropylmethyldimethoxysilane

[Chemical Formula 12]

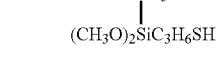

2-(3,4epoxycyclohexyl)ethyltrimethoxysilane

[Chemical Formula 13]

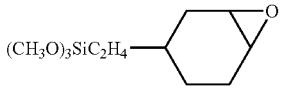

3-Glycidoxypropyltrimethoxysilane

[Chemical Formula 14]

3-Glycidoxypropylmethyldiethoxysilane

[Chemical Formula 15]

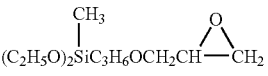

3-Glycidoxypropyltriethoxysilane

The silane coupling agent (a) is preferably a compound represented by the general formula [1] in which R1 is an organic residue having at least one functional group selected from the group consisting of a (meth)acryloyl group and a vinyl group, R2 is a hydroxyl group, an alkyl group having 1 to 5 carbon atoms or an alkoxy group having 1 to 5 carbon atoms, and R3 and R4 each is a hydroxyl group or an alkoxy group having 1 to 5 carbon atoms.

Particularly preferred silane coupling agents (a) are 3-methacryloxypropylmethyldimethoxysilane, 3-methacryloxypropyltrimethoxysilane, 3-methacryloxypropylmethyldiethoxysilane, 3-methacryloxypropyltriethoxysilane and 3-acryloxypropyltrimethoxysilane.

The proportion of the silane coupling agent (a) can appropriately vary depending on the use purpose of the composition, and is preferably within a range from 1.0 to 40.0 parts by weight.

The weak acidic compound (b) is in the form of an aqueous solution and has an acid dissociation exponent pKa of 3 or more, and examples thereof include formic acid, acetic acid, propionic acid, benzoic acid, phenol, and carbonic acid.

The proportion of the weak acidic compound (b) can appropriately vary depending on the use purpose of the composition, and is preferably within a range from 0.01 to 0.4 part by weight.

The strong acidic compound (c) is in the form of an aqueous solution and has an acid dissociation exponent pKa of less than 3, and examples thereof include HF, HCl, HBr, HI, $HNO_3$, $HClO_3$, $HClO_4$, $HBrO_4$, $HMnO_4$, $H_2SO_4$, and $H_3PO_4$.

The proportion of the strong acidic compound (c) can appropriately vary depending on the use purpose of the composition, and is preferably within a range from 0.01 to 0.4 part by weight.

Examples of the volatile organic solvent (e) in the present invention include methanol, ethanol, isopropanol, butanol, acetone, ethyl acetate, isopropylether, and a radical polymerizable monomer such as a (meth)acrylic acid ester, (meth)acrylamide, and a vinyl ester.

The volatile organic solvent is preferably ethanol or acetone, and the proportion of the volatile organic solvent (e) can appropriately vary depending on the use purpose of the composition, and is preferably within a range from 20.0 to 99.0 parts by weight.

The dental adhesive composition of the present invention essentially contains the silane coupling agent (a), the weak acidic compound (b), the strong acidic compound (c), water (d) and the volatile organic solvent (e), and other components can be added by appropriate selection. Depending on the use purpose, additive components such as a radical polymerizable monomer, a photopolymerization initiator, a photopolymerization accelerator, a thermopolymerization initiator, a polymerization catalyst, inorganic and organic fillers, a polymerization inhibitor, and a pigment can be appropriately mixed.

To the dental adhesive composition in the present invention, a radical polymerizable monomer can be added. Specific examples of the radical polymerizable monomer include (meth)acrylic acid, (meth)acrylate such as methyl (meth)acrylate or ethyl(meth)acrylate and a modified monomer thereof in which a hydroxyl group or halogen is substituted on an alkyl side chain, methoxydiethylene glycol (meth)acrylate, methoxypolyethylene glycol (meth)acrylate, ethylene glycol di(meth)acrylate, triethylene glycol di(meth)acrylate, tetraethylene glycol di(meth)acrylate, hexamethylene glycol di(meth)acrylate, polyethylene glycol di(meth)acrylate, propylene glycol di(meth)acrylate, polypropylene glycol di(meth)acrylate, neopentyl glycol di(meth)acrylate, 2,2'-bis{4-(meth)acryloxypropoxyphenyl}propane, 2,2'-bis{4-(meth)acryloxyethoxyphenyl}propane, 2,2'-bis{4-(meth)acryloxydiethoxyphenyl}propane, bisphenol A di(meth)acrylate, bisphenol A diglycidyl(meth)acrylate, trimethylolpropane tri(meth)acrylate, trimethylolethane tri(meth)acrylate, tetramethylolethane tetra(meth)acrylate, epoxy-(meth)acrylate, urethane (meth)acrylates which is a reaction product of an organic diisocyanate and oxyalkyl (meth)acrylate, a polymerizable prepolymer having at least two polymerizable ethylenically unsaturated groups which is a reaction product of a urethane prepolymer (a reaction product of an organic diisocyanate and diol) and a (meth)acrylic acid ester of oxyalkanol having at least two carbon atom, and a reaction product of a dibasic carboxylic acid having an ethylenically unsaturated group and a dihydric alcohol (i.e., a polyester having an ethylenically unsaturated group).

These radical polymerizable monomers may be used alone, or appropriately used in combination. Among these, a combination of bisphenol A diglycidyl(meth)acrylate of a polymerizable monomer such as di(meth)acrylate and triethylene glycol di(meth)acrylate is preferred.

As the polymerization initiator in the present invention, a known compound used generally for a dental composition is used without any limitation. The polymerization initiator is generally classified into a thermopolymerization initiator and a photopolymerization initiator.

It is possible to use, as the photopolymerization initiator, a photosensitizer which generates a radical upon irradiation with light. Examples of the photosensitizer to ultraviolet rays include benzoin compound-based compounds such as benzoin, benzoin methyl ether, and benzoin ethyl ether; benzophenone-based compounds such as acetoinbenzophenone, p-chlorobenzophenone, and p-methoxybenzophenone; and thioxanthone-based compounds such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, and 2,4-diisopropylthioxanthone. A photosensitizer which initiates polymerization upon irradiation with visible rays is preferably used since it does not require ultraviolet rays which are harmful for the human body. Examples thereof include a-diketones such as benzil, camphorquinone, a-naphthil, acetonaphthene, p,p'-dimethoxybenzil, p,p'-dichlorobenzylacetil, pentanedion, 1,2-phenanthrenequinone, 1,4-phenanthrenequinone, 3,4-phenanthrenequinone, 9,10-phenanthrenequinone, and naphthoquinone. Preferably, camphorquinone is used.

It is also preferred to use the photosensitizer in combination with a photopolymerization accelerator. When a tertiary amine is used as the photopolymerization accelerator, it is more preferred to use a compound in which nitrogen atoms are directly substituted on aromatic groups. It is possible to use, as the photopolymerization accelerator, tertiary amines such as N,N-dimethylaniline, N,N-diethylaniline, N,N-di-n-butylaniline, N,N-dibenzylaniline, N,N-dimethyl-p-toluidine, N,N-dimethyl-m-toluidine, N,N-diethyl-p-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, N,N-dihydroxyethyl-p-toluidine, p-dimethylaminophenyl alcohol, p-dimethylaminostyrene, N,N-dimethyl-3,5-xylydine, 4-dimethylaminopyridine, N,N-dimethyl-a-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino)dimethanol; barbituric acids such as 5-butylbarbituric acid, and 1-benzyl-5-phenylbarbituric acid, and metal salts thereof such as a sodium salt, and a calcium salt; and tin compounds such as dibutyltin diacetate, dibutyltin dimaleate, dioctyltin dimaleate, dioctyltin dilaurate, dibutyltin dilaurate, dioctyltin diversatate, dioctyltin-S,S'-bis-isooctylmercapto acetate, and tetramethyl-1,3-diacetoxydistannoxane. At least one kind selected from among these photopolymerization accelerators can be used, and also a mixture of two kinds of them can be used. The addition amount of the initiator and accelerator can be appropriately determined.

Furthermore, for the purpose of improving photopolymerization acceleration ability, it is effective to add, in addition to the tertiary amine, oxycarboxylic acids such as citric acid, malic acid, tartaric acid, glycolic acid, gluconic acid, a-oxyisobutyric acid, 2-hydroxypropanoic acid, 3-hydroxypropanoic acid, 3-hydroxybutanoic acid, 4-hydroxybutanoic acid, and dimethylolpropionic acid.

Specifically, as the thermopolymerization initiator, organic peroxides such as benzoyl peroxide, parachlorobenzoyl peroxide, 2,4-dichlorobenzoyl peroxide, acetyl peroxide, lauroyl peroxide, tertiary butyl peroxide, cumen hydroperoxide, 2,5-dimethylhexane-2,5-dihydro peroxide, methyl ethyl ketone peroxide, and tertiary butylperoxybenzoate; and azo compounds such as azobisisobutyronitrile, methyl azobisisobutyrate, and azobiscyanovaleric acid are preferably used.

The polymerization can be performed at a normal temperature by using the organic peroxide in combination with an amine compound. As the amine compound, a secondary or tertiary amine in which amine groups are bonded to aryl groups are preferably used in view of acceleration of curing. For example, N,N-dimethyl-p-toluidine, N,N-dimethylaniline, N,N-β-hydroxyethyl-aniline, N,N-di(β-hydroxyethyl)-aniline, N,N-di(β-hydroxyethyl)-p-toluidine, N-methyl-aniline and N-methyl-p-toluidine are preferred.

It is also preferred to further use the combination of the organic peroxide and the amine compound in combination with sulfinate or boride. Examples of the sulfonate include sodium benzenesulfinate, lithium benzenesulfinate, and sodium p-toluenesulfonate. Examples of the boride include a sodium salt, a lithium salt, a potassium salt, a magnesium salt, a tetrabutylammonium salt, and a tetramethylammonium salt of trialkylphenylboron and trialkyl(p-fluorophenyl)boron (alkyl group is an n-butyl group, an n-octyl group, an n-dodecyl group, etc.). Organoboron compounds which react with oxygen or water to generate a radical, such as tributylborane, and tributylborane partial oxide can also be used as an organometal type polymerization initiator.

If necessary, the dental adhesive composition of the present invention can be mixed with known various additives. Examples of the additive include a polymerization inhibitor, a coloring agent, a discoloration inhibitor, a fluorescent agent, an ultraviolet absorber, and an antibacterial agent.

Examples of the inorganic and organic fillers include organic polymer powders made of polymethyl methacrylate, polyethyl methacrylate, a copolymer of methyl methacrylate and ethyl methacrylate, and polystyrene; organic fillers obtained by grinding a thermocurable resin cured article or a thermocurable resin cured article containing an inorganic filler; inorganic fillers (kaolin, talc, quartz, silica, colloidal silica, alumina, aluminosilicate, silicon nitride, magnesium sulfate, calcium phosphate, barium sulfate, glass powder, etc.), and composite fillers of inorganic fillers and organic fillers, which are suited for use of the composition in the form of a powder/liquid, paste or slurry. A surface of these fillers may be coated with a coupling agent having a silanol group (γ-methacryloxypropyltrimethoxysilane, etc.).

Examples of the polymerization inhibitor include hydroquinone, hydroquinone monomethyl ether, and butylated hydroxytoluen, which are suited for stabilization of shelf-life of the composition.

EXAMPLES

The present invention will be specifically explained by way of Examples, but the present invention is not limited to the following Examples.

Abbreviations (Chemical Names) Shown in Examples

1) Silane coupling agent

3-MPTES: 3-Methacryloxypropyltriethoxysilane

2) Radical polymerizable monomer

Bis-GMA: Bisphenol A diglycidyl methacrylate

3G: Triethylene glycol dimethacrylate

3) Photopolymerization initiator, Photopolymerization accelerator

CQ: Camphorquinone

DMBE: Ethyl p-dimethylaminobenzoate

4) Filler

R-972: Silicic acid fine particle [manufactured by NIPPON AEROSIL CO., LTD.]

Materials and Apparatuses used in Test

Resin cement: "ResiCem" [manufactured by SHOFU INC.]

Porcelain disk-shaped plate: 15.0 mm in diameter×5.0 mm [dental porcelain for baking onto metal [trade name "Vintage Halo" (manufactured by SHOFU INC.)]]

Gold alloy plate: about 15×15×2 mm [trade name "SUPER GOLD 4" (manufactured by SHOFU INC.)]

Instron Universal Testing Machine [manufactured by INSTRON CO.]

Examples of Dental Primer or Dental Adhesive Material

Preparation of Adhesive Composition (a) Silane coupling agent: 3MPTES (b) Weak acidic compound: Acetic acid (d) Water According to each formulation shown in Table 1 and Table 2, above components were mixed with shaking for 5 minutes and heat generation of the obtained mixed solution was confirmed. The mixed solution was allowed to stand under sealed condition at 23° C. for 24 hours to obtain a mixed solution A1 and a mixed solution A2.

TABLE 1

(Mixed solution A1)

| Components | Amount (parts by weight) |
| --- | --- |
| (a) 3MPTES | 100.0 |
| (b) Acetic acid | 1.0 |
| (d) Water | 10.0 |
| (e) Ethanol | 9.0 |

TABLE 2

(Mixed solution A2)

| Components | Amount (parts by weight) |
| --- | --- |
| (a) 3MPTES | 100.0 |
| (b) Formic acid | 1.0 |
| (d) Water | 10.0 |
| (e) Ethanol | 9.0 |

Then, 37 parts by weight of an aqueous phosphorus solution was added to a mixed solution A in Table 1 according to the formulation shown in Table 3, followed by mixing with shaking for 5 minutes. Heat generation of the obtained mixed solution was confirmed. The mixed solution is referred to as mixed solution B1.

TABLE 3

| Components | Amount (parts by weight) |
| --- | --- |
| Mixed solution A | 120.0 |
| (c) 37 parts by weight of aqueous phosphoric acid solution | 2.5 |

A mixed solution prepared by using a mixed solution shown in Table 2 in place of the mixed solution shown in Table 1 to be added according to the formulation shown in Table 3 was referred to as mixed solution B2.

Then, ethanol was added to the mixed solution B1 according to the formulation shown in Table 4, followed by mixing with shaking for 5 minutes to prepare an adhesive composition.

TABLE 4

| Examples or Comparative Examples | Component, Proportion (parts by weight) | |
| --- | --- | --- |
| | Mixed solution B | Ethanol |
| Example 1 | 2.5 | 97.5 |
| Example 2 | 6.5 | 93.5 |
| Example 3 | 16.0 | 84.0 |
| Example 4 | 40.0 | 60.0 |
| Comparative Example 1 | 100.0 | 0.0 |

An adhesive composition was prepared by using the mixed solution B2 in place of the mixed solution to be mixed in the proportion shown in Table 4. In Table 5, the adhesive composition is described.

TABLE 5

| Examples or Comparative Examples | Component, Proportion (parts by weight) | |
| --- | --- | --- |
| | Mixed solution B | Ethanol |
| Example 5 | 2.5 | 97.5 |
| Example 6 | 6.5 | 93.5 |
| Example 7 | 16.0 | 84.0 |
| Example 8 | 40.0 | 60.0 |

(Tensile Adhesion Test)

As an example of a dental ceramic material, a disk-shaped (15.0 mm in diameter×5.0 mm) baked product was made from a dental porcelain for metal baking [trade name "Vintage Halo" (manufactured by SHOFU INC.)] using a vacuum electric furnace for porcelain baking [trade name "Twinmat" (manufactured by SHOFU INC.)], and a test of a tensile adhesive strength was carried out.

A flat surface of the disk-shaped (15.0 mm in diameter×5.0 mm) baked product was polished using #240 and #600 silicone carbide papers [manufactured by Sankyo-Rikagaku Co., Ltd.] under running water to obtain a smooth surface. After ultrasonic wave cleaning and air drying, an adherend was obtained. On an adhesive surface of the adherend, an adhesive composition was applied using a mini brush, allowed to stand at it is for 30 seconds and then dried using an air syringe so that fluidity of the adhesive composition disappeared. Separately, an adhesive surface of a cylindrical Cobaltan (cobalt chromium alloy: manufactured by SHOFU INC.) rod, 5 mm in diameter×10 mm in height, was subjected to air ablation (50 μm alumina beads, pressure of 5 kgf/cm$^2$), followed by ultrasonic wave cleaning and air drying to obtain a jig for measurement of an adhesive strength. Bonding was performed by allowing "ResiCem" kneaded in the form of a uniform paste to exist on the adhesive surface of the adherend and the adhesive surface of the stainless steel rod. In this case, an excess cement was removed by a mini brush and a cement margin was photopolymerized for 10 seconds using "Shofu Grip Light II". All seven test pieces were immersed in water at 37° C. and the tensile adhesive strength was measured after dipping in water at 37° C. for 24 hours. In the measurement of the adhesive strength, the tensile adhesive strength was measured under the conditions of a crosshead speed of 1 mm/min using Universal Testing Machine (manufactured by INSTRON CO.). The entire adhesion test was carried out at room temperature of 23° C.±1° C.

The tensile adhesive strength measured, in the case that the adhesive composition was prepared and used within 24 hours under a storage environment at 23° C. in a sealed state, was referred to as "initial" tensile adhesive strength. The tensile adhesive strengths, in the case that the adhesive composition was prepared and used after storage for 1, 2 and 3 months under a storage environment at 50° C. in a sealed state, were referred to as tensile adhesive strengths "after storage 50° C. for 1, 2 and 3 months", respectively. The results are shown in Table 6.

TABLE 6

| Adhesive composition | Tensile adhesive strength/MPa | | | |
| --- | --- | --- | --- | --- |
| | Initial | After storage at 50° C. for 1 month | After storage at 50° C. for 2 months | After storage at 50° C. for 3 months |
| Example 1 | 11.8 | 16.6 | 13.4 | 10.4 |
| Example 2 | 16.2 | 17.1 | 15.4 | 10.8 |
| Example 3 | 17.9 | 17.1 | 17.3 | 11.4 |
| Example 4 | 16.7 | 20.7 | 19.3 | 14.4 |
| Example 5 | 11.0 | 14.2 | 12.4 | 11.9 |
| Example 6 | 15.2 | 15.1 | 14.5 | 12.8 |
| Example 7 | 16.9 | 15.1 | 16.3 | 11.2 |
| Example 8 | 16.5 | 18.7 | 18.3 | 13.7 |
| Comparative Example 1 | 17.8 | 13.1 | 9.7 | 4.8 |

As is apparent from the results shown in Table 6, the adhesive composition of the present invention exhibits excellent adhesion even after lapse of time.

What is claimed is:

1. A one-pack dental adhesive composition comprising: (a) a silane coupling agent, (b) a weak acidic compound, which is organic acid, and has an acid dissociation exponent pKa of 3 or more in the form of an aqueous solution, (c) a strong acidic compound which is $H_3PO_4$ and has an acid disassociation exponent pKa of less than 3, (d) water and (e) a volatile organic solvent, at a ratio by weight of (a):(b):(c):(d):(e)=1.0 to 40.0 parts by weight: 0.01 to 0.4 part by weight: 0.01 to 0.4 part by weight: 0.1-5.0 parts by weight: 20.0 to 99.0 parts by weight, wherein the silane coupling agent is in admixture with the organic acid, the $H_3PO_4$, the water and the volatile organic solvent.

* * * * *